United States Patent [19]

Ljungström

[11] Patent Number: 5,669,392
[45] Date of Patent: Sep. 23, 1997

[54] DEVICE FOR VARYING THE THRESHOLD DETECTION LEVEL OF A SENSOR

[75] Inventor: Jan Ljungström, Hässelby, Sweden

[73] Assignee: Pacesetter AB, Solna, Sweden

[21] Appl. No.: 673,114

[22] Filed: Jul. 1, 1996

[30] Foreign Application Priority Data

Jul. 4, 1995 [SE] Sweden ................... 9502430

[51] Int. Cl.$^6$ ................................... A61B 5/0402
[52] U.S. Cl. .............. 128/704; 128/708; 128/672; 128/687; 128/716; 128/736; 607/17
[58] Field of Search ................... 128/630, 668, 128/672, 687, 696, 697, 704, 708, 716, 736, 901, 902; 607/17; 364/413.03, 413.05, 413.06

[56] References Cited

U.S. PATENT DOCUMENTS

| | | | |
|---|---|---|---|
| 4,708,144 | 11/1987 | Hamiton et al. | |
| 5,050,599 | 9/1991 | Hoegnelid | 607/17 |
| 5,370,124 | 12/1994 | Dissing et al. | 128/696 |
| 5,374,282 | 12/1994 | Nichols et al. | 607/18 |
| 5,388,586 | 2/1995 | Lee et al. | 128/704 |
| 5,423,870 | 6/1995 | Olive et al. | 607/18 |
| 5,448,997 | 9/1995 | Kruse et al. | 128/697 |

FOREIGN PATENT DOCUMENTS

| | | |
|---|---|---|
| 0 321 764 | 6/1989 | European Pat. Off. |
| 0 600 200 A1 | 8/1994 | European Pat. Off. |

Primary Examiner—Jeffrey R. Jastrzab
Attorney, Agent, or Firm—Hill, Steadman & Simpson

[57] ABSTRACT

In a method and apparatus for automatically adjusting the threshold detection level of a detector unit for detecting physiological events, e.g. heart contractions, a cardiac signal is sensed and sampled, the samples of the cardiac signal are stored in a memory. A timer starts the sampling and stops the sampling after a predetermined time. An analysis unit analyzes the stored cardiac signal samples to generate a first set of values which represent physiological events, such as average peak signal value, the average maximum signal slope or an integrated signal value. The analysis unit calculates at least one derived parameter from the whole of the first set of values and automatically determines a new threshold detection level for the sensor as a function of this at least one derived parameter. For this purpose the analysis unit (8) compares the new threshold detection level with the stored periodic physiological signal to determine how many physiological events would have been detected if the new threshold level had been in use when the sampling was taking place, and the analysis unit changes the new threshold detection level if the number of physiological events which would have been detected differs by more than a programmable number from the estimated number of physiological events.

38 Claims, 2 Drawing Sheets

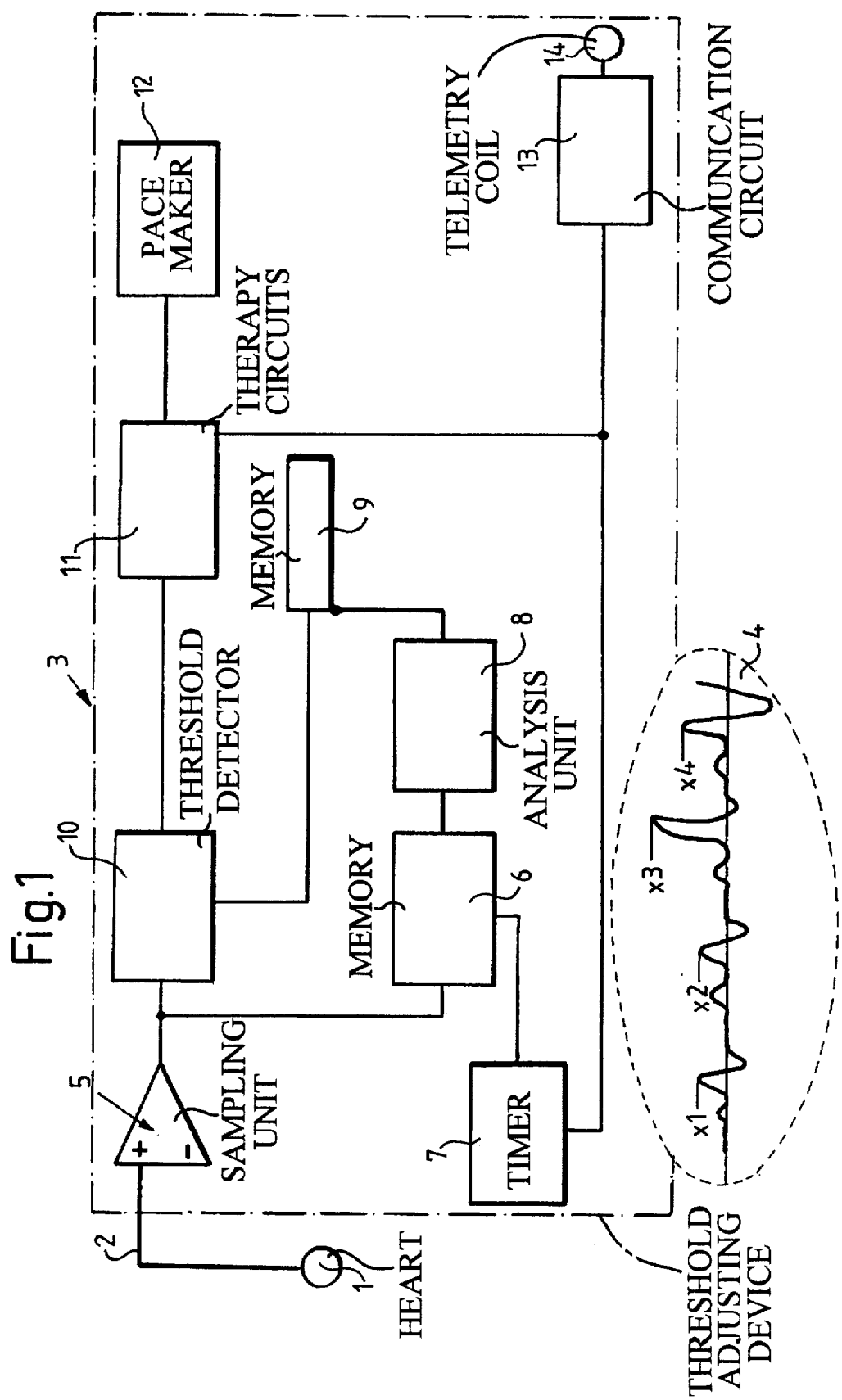

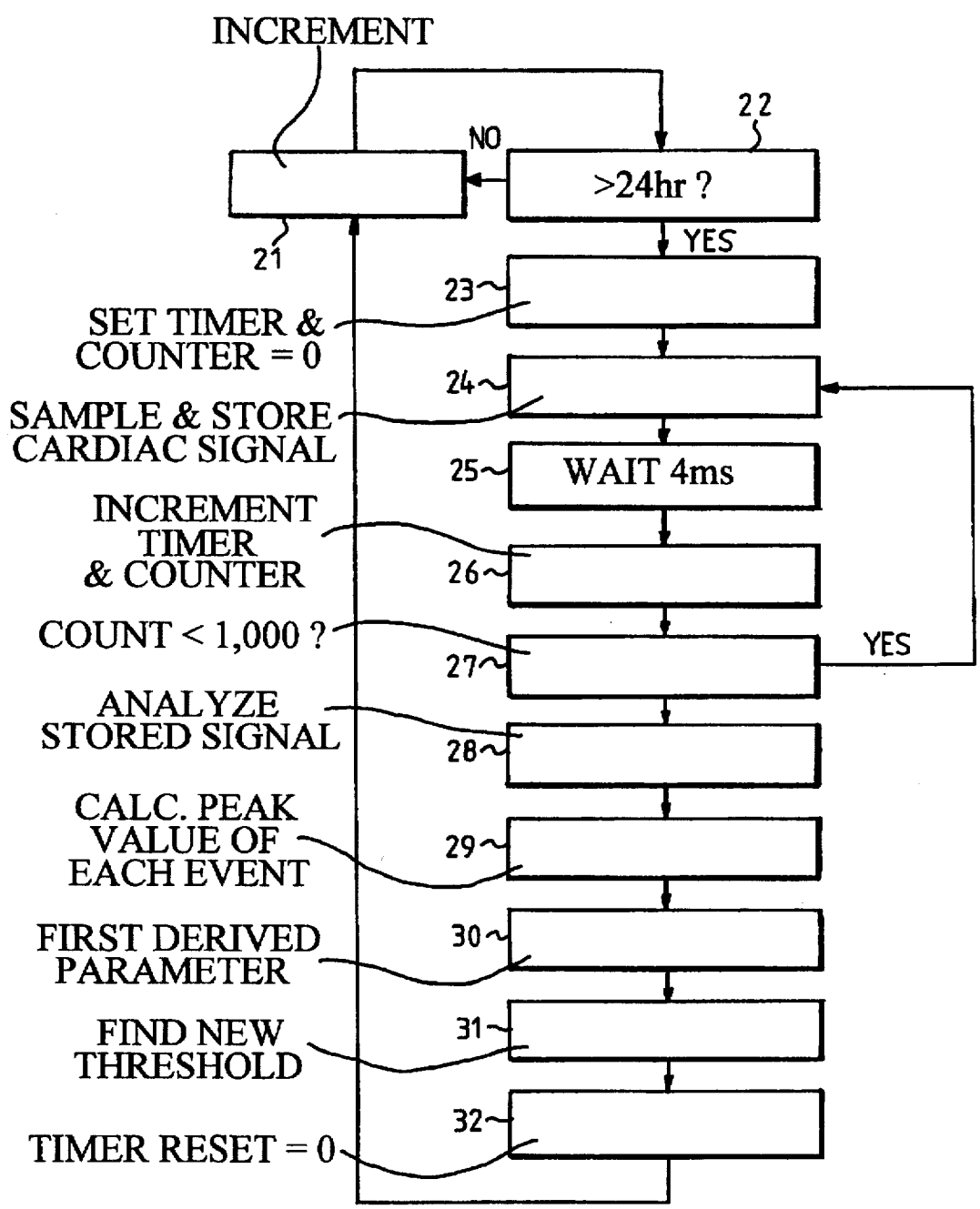

DEVICE FOR VARYING THE THRESHOLD DETECTION LEVEL OF A SENSOR

BACKGROUND OF THE INVENTION

1. Field of the Invention

The invention relates to a device for adjusting the threshold detection level of a sensor, particularly a sensor for sensing physiological signals for use with an implantable pacemaker or cardiac diagnostic device, to take into account the level of the sensed signal.

2. Description of the Prior Art

Sensors are used medically to detect signals which relate to the physiological activity of a subject and which can be used to aid diagnosis or treatment. Various different parameters can be measured, for example, pulse rate, respiration rate, blood pressure, temperature, etc. The choice of which parameter or parameters to detect is decided by a physician and is adapted to the specific circumstances of each subject.

Sensors can be used to detect the cardiac activity of pacemaker users by measuring the electrical signals produced by the heart when it beats. Each heart contraction is preceded by an electrical pulse and the detection of these electrical pulses is used to control pacemakers. To avoid noise and signals generated by non-cardiac muscle activity being erroneously sensed as a cardiac event, it is usual to set a sensor threshold detection level below which all signals are ignored. The choice of threshold detection level is of critical importance. Setting the threshold detection level too high can result in "undersensing"—a condition where cardiac events are not sensed which could mean that the pacemaker loses synchronization with the intended natural cardiac rhythm or delivers extra pacing stimuli at inappropriate times, for example, just after a successful capture which was not sensed. Setting the threshold detection level too low will result in non-cardiac electrical activity erroneously being sensed as cardiac events. This is known as "oversensing" and can lead to the pacemaker delivering stimulation pulses at inappropriate times, can cause high pacing rates and can lead to pacemaker-mediated tachycardia. Hence it is important that a correct threshold detection level is set.

Unfortunately the impedance of the signal path in the patient body varies considerably as time passes. This change in impedance affects the amplitude of the signal and the sensor sensitivity has to be adjusted to take account of this change. Long term changes, over a period of days, weeks or months can be caused by lead maturation or chronic changes in cardiac activity, while short term changes occur between heart beats and can be caused by changes in the patient's activity or changes in the chest shape due to respiration.

A method for adjusting the sensor sensitivity is disclosed in U.S. Pat. No. 4,708,144 which describes a method of calculating the average peak amplitude of a cardiac signal over a period of minutes and subsequently varying the amplification of the cardiac signal in accordance with the average peak amplitude. Because the average peak amplitude is calculated over a period of minutes, this method reacts slowly to changes in the peak amplitude and cannot take into account beat-to-beat variations in cardiac activity.

European Application 580 894 describes a method for adjusting the threshold of a sensor when the running average value over, for example, 18 heart beats, of the margin by which a measured signal exceeds a lower threshold falls outside upper and lower boundaries. Once this occurs a new threshold is established with new upper and lower boundaries. The requirement that the average value must first fall outside the region between the upper and lower boundaries means that the reaction to changes in the signal takes place after a delay and in a step like fashion. This method cannot take into account beat-to-beat variations in cardiac activity. Furthermore, the use of a running average means that only a small amount of the total information in the signal is stored and hence is available for analysis, and therefore more sophisticated analysis of the stored signal is not possible.

SUMMARY OF THE INVENTION

An object of the present invention is to provide a method and apparatus for automatically adjusting the sensitivity of a sensing device for an implantable pacemaker in which the beat-to-beat variations in sensed cardiac activity are taken into account.

This object is achieved in accordance with the principles of the present invention in a method and apparatus wherein sensing is controlled by circuitry which stores samples representing a small number of cardiac events and analyses the stored signal to calculate a new threshold 10 detection level.

DESCRIPTION OF THE DRAWINGS

FIG. 1 is a diagram of a threshold adjusting device in accordance with one embodiment of the present invention.

FIG. 2 is a flow diagram according to one embodiment of the present invention.

DESCRIPTION OF THE PREFERRED EMBODIMENTS

A first embodiment of a sensing device for a pacemaker according to the invention contains circuitry for sampling an input signal, timer means for starting the sampling and stopping the sampling after a predetermined time, a memory for storing the input signal samples, an analyzing means for analyzing the input signal samples to generate a first set of values representing cardiac events, calculating means for calculating a threshold detection level and means for producing an output when the input signal fulfils certain conditions. It also contains communication means by which it can be programmed by a physician or technician and by means of which it can pass information to a physician or technician.

In this embodiment the sensing device is illustrated as being connectable to a lead which picks up electrical signals from the heart, however, any other appropriate signal which changes in relation to heart activity, e.g., blood pressure, blood oxygen level or temperature could be used. The signal is sampled at regular intervals in order to detect cardiac events. The analyzing circuitry analyses the signal to determine when a cardiac event has probably taken place. One way of determining if a cardiac event has occurred is to set various conditions which must be fulfilled before a signal is accepted as representing a cardiac event. An example of such conditions would be that after a candidate for evaluation as a cardiac event has been determined to have taken place, the signal must first go to below zero, then reach a peak which is above the sensor threshold and finally drop to zero again once these conditions have been achieved it is assumed that a cardiac event has occurred and this information is used by the pacemaker to control its pacing.

In a first embodiment of the invention the sensor threshold can automatically be adjusted in response to variations in the peak value of the input signal. This is achieved by storing the samples of the input signal and analyzing them. In order to reduce cost the samples can be stored in a small memory which can store only a limited number of samples and a limited number of signal levels. Typically, samples could be taken every 4 mS for 4 seconds and the signal resolution limited to an 8 bit value for each sample. The timing means controls the storing of the input signal and can be programmed to continuously store the most recent samples or can be programmed to only store samples at certain intervals e.g. once an hour, once a day, once every 36 hours, once a week, once a month, etc. Once the samples have been stored the analysis means analyses the stored signal values using, for example, the above mentioned conditions to find out how many cardiac events took place in the 4 seconds and to determine the peak signal level associated with each cardiac event. Each of these peak signal levels are stored and together they form a set of first representative values representing cardiac events. A derived parameter which can be used to represent the stored signal is then derived from the set of first representative values. In this first embodiment the derived parameter is the average value of the set of first representative values; other derived parameters could be the maximum slope of the curve representing a cardiac event, or an integrated value such as the area under the curve, or any other such parameter. The threshold detection level is then set at a level which is a predetermined or programmable function of the derived parameter, or the level can be found from a look-up table.

FIG. 1 shows a diagram representing a threshold adjusting device in accordance with one embodiment of the present invention. The device shown can be built into a pacemaker or made as a separate unit. A heart 1 is connected by an electrode cable 2 to a threshold adjusting device 3. The electrode cable 2 carries a signal 4 which represents cardiac activity. The signal 4 shows in FIG. 1 how the amplitude of the electrical signal from the heart varies with respect to time. The signal 4 shows four QRS signals which have different maximum values, x1, x2, x3, x4. The signal 4 is sampled by a sampling unit 5, which could be an A/D converter, and the digital signal is stored in a memory 6 at an interval controlled by a timer 7. The stored signal is analyzed, in a manner described later, by an analysis unit 8, which can be a microprocessor or similar device, to determine a new detector threshold value. The memory 6 may be a RAM and can be internal or external to the microprocessor 8. The memory 6 contains the operating commands for instructing the analysis unit 8 how to perform the analysis of the cardiac signal and subsequently to control the variation in the sensor threshold detection level. A memory 9 stores the detector threshold values calculated by the analysis unit 8. It can also contain a look-up table of sensor threshold detection levels. A detector threshold value from the memory is communicated to threshold detector 10 which filters the digital signal from the sampling unit 5 before sending the signal to therapy circuits 11. The therapy circuits 11 control the functioning of a pacemaker 12.

In the embodiment shown in FIG. 1 the threshold adjusting device 3 has a communication circuit 13 connected to a telemetry coil 14 for sending signals to, and receiving signals from, an extracorporeal programmer. This allows the device to be reprogrammed and also to transmit stored information for further analysis as necessary.

FIG. 2 shows a flow diagram for a microprocessor-based circuit for adjusting a sensor threshold detection level every 24 hours. The steps in the flow diagram of FIG. 2 are performed in the analysis unit 8 with access to the memory 6.

In this embodiment analysis unit 8 has a counter S which is incremented by one every second at stage 21. The counter S records the time S which has elapsed since the last time the threshold detection level was adjusted. The counter S is monitored by the analysis unit 8 at stage 22 and when the counter S reaches 86 400, which means 24 hours have elapsed, the analysis unit 8 sets a timer T to zero and another counter N to zero at stage 23. At stage 24 the cardiac signal is sampled and its amplitude is stored in a memory M in space number N. The analysis unit 8 waits 4 mS at stage 25 and then increments both the timer T and the counter N by one at stage 26. Stage 27 checks how many samples have been made. If the count of the counter N is less than 1000 then the analysis unit 8 returns to stage 24 and makes another sample. If the counter N has reached 1000 then the sampling is stopped and the stored signal is analyzed at stage 28 to identify cardiac events as explained previously. The peak signal value (x1, x2, x3, x4 . . . xn) is calculated for each event at stage 29 and a first derived parameter, such as the average peak signal value, is calculated at stage 30. The analysis unit 8 finds the new sensor detector threshold at stage 31 by looking up in a look-up table the sensor detector threshold level which corresponds to the calculated average peak signal value and the threshold detector level is set to the new level. The timer S is reset to zero at stage 32 and the cycle starts again from stage 21.

Instead of, or in addition to, the peak signal value (xn) some other-value such as the maximum positive or negative slope, could be determined from the stored signal value and used as a second representative value to represent the occurrence of a cardiac event. A second derived parameter representing, for example, the average value of these second representative values for the stored cardiac events could be calculated and the threshold detection level then set at a level which is a predetermined or programmable function of the second derived variable or the level can be found from a look-up table.

In another embodiment of the invention representative values are compared against the average value and the representative value which differs most from the average value is ignored and a new average value calculated. The threshold detection level is then set at a level which is a predetermined or programmable proportion of the latter average value or the level can be found from a look-up table.

In a further embodiment of the invention the representative value which is highest (e.g. x3 in FIG. 1) is ignored when the average value is calculated. As before, the threshold detection level is set at a level which is a predetermined or 10 programmable proportion of the average value or the level can be found from a look-up table.

It is of course possible to calculate more derived parameters and to use a combination of two or more of them to establish 15 the new threshold detection level.

In a particularly advantageous embodiment of the invention the new threshold detection level is tested against the stored signal to check that it is appropriate. For example, if the stored signal contains four detected peaks which are separated by approximately equal time intervals, it is reasonable to assume that exactly four events occurred in the time period covered by the stored signal and that all four of them were detected. The stored signal is then compared with the new threshold detection level to determine how many events would have been detected if the new threshold detection level had been used. If less than four events would have been detected with the new threshold detection level, then the threshold level can be considered to be too high. If five or more events would have been detected then the new threshold detection level can be considered to be too low. In each of these two cases an amended new threshold detection level can be set which could be a proportion, e.g., 90% or 95%, or 105% or 110%, of the new threshold detection level and this amended new threshold detection level can be compared with the stored signal to determine how may events would have been detected if the new threshold detection level had been used. This can be repeated until a threshold detection level which would have detected exactly four events is achieved. The threshold detector level is then set at this level.

Alternatively a number of new threshold detector levels can be set by analysis of one or more of the derived parameters. These new threshold detector levels could then each be compared against the stored signal to determine which gives the best result and the threshold set at this level.

In some cases of irregular heartbeat or large differences in the magnitude of detected signals, it is not always possible to be sure how exactly many events occurred in the time period covered by the stored signal. For example, depending on where the threshold detector level is set it could appear that 4 or 5 events would have been detected and a low level where, for example, 5 events would have been detected. This calculated threshold detection level could be a simple or weighted average of the high and low levels or some other appropriate proportion of the difference between the two levels.

Another way of determining the threshold detector level is to set the level as a programmable proportion of a peak value of the stored signal. For example, the level could be set at 40% of the third highest peak or 30% of the second value peak. This level could then be compared with the stored signal to determine how many detections would have been made if this level had been used when the signal was recorded. An acceptable number of detections can be prescribed, for example, by programming in numbers corresponding to upper and lower acceptance limits, e.g., a maximum of 6 detections and a minimum of 3 detections. In this example, if the number of detections fall outside this range then the level is changed to lower value if less than 3 detections would have been made and the level is changed to higher value if more than 6 detections would have been made.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical diagnostic device comprising:
    sensor means for sensing a periodic physiological signal, representing physiological events, from a living subject;
    sampling means, connected to said sensor means, for collecting samples of said periodic physiological signal employing a threshold detection level;
    memory means for storing said samples of said periodic physiological signal;
    timer means for starting said sampling means and for stopping said sampling means after a predetermined time;
    analysis means having access to said memory means for analyzing said periodic physiological signal using the samples stored in said memory means by estimating a number of said physiological events occurring in said periodic physiological signal during said time and for generating a set of values corresponding to said physiological events;
    said analysis means including means for calculating at least one derived parameter from said set of values; and
    said analysis means including means for automatically determining a new threshold detection level for said sampling means as a function of said at least one derived parameter and means for comparing said new threshold detection level with the samples stored in said memory means for determining how many of said physiological events would have been detected if said new threshold detection level had been used by said sampling means, and for changing said threshold detection level of said sampling means to said new threshold detection level if the number of physiological events which would have been detected differs by more than a programmable number from said estimated number of physiological events.

2. A medical diagnostic device as claimed in claim 1 wherein said set of values comprises a first set of values, and said analysis means further including:
    discriminating means for ignoring at least one value of said first set of values and for forming a second set of values comprising said first set of values without said at least one value;
    means for calculating at least one auxiliary derived parameter from said second set of values; and
    means for automatically varying said threshold detection level of said sensor means as a function of said at least one auxiliary derived parameter and said derived parameter.

3. A medical diagnostic device as claimed in claim 2 wherein said means for calculating at least one auxiliary derived parameter from said second set of values comprises means for determining an average peak signal value.

4. A medical diagnostic device as claimed in claim 2 wherein said means for calculating at least one auxiliary derived parameter from said second set of values comprises means for determining an average maximum signal slope.

5. A medical diagnostic device as claimed in claim 2 wherein said means for calculating at least one auxiliary derived parameter from said second set of values comprises means for determining an integrated signal value.

6. A medical diagnostic device as claimed in claim 2 wherein said discriminating means comprises means for ignoring a maximum value in said first set of values.

7. A medical diagnostic device as claimed in claim 2 wherein said discriminating means comprises means for ignoring a minimum value in said first set of values.

8. A medical diagnostic device as claimed in claim 2 wherein said discriminating means comprises means for determining an average value of said first set of values and means for ignoring a value of said first set of values which is farthest from said average value.

9. A medical diagnostic device as claimed in claim 1 wherein said sensor means comprise means for sensing a cardiac signal, representing cardiac events, from said living subject and wherein said analysis means estimates a number of said cardiac events.

10. A medical diagnostic device comprising:
    sensor means, having a threshold detection level associated therewith, for sensing a periodic physiological signal, representing physiological events, from a living subject;
    sampling means, connected to said sensor means, for collecting samples of said periodic physiological signal employing a threshold detection level;

memory means for storing said samples of said periodic physiological signal;

timer means for starting said sampling means and for stopping said sampling means after a predetermined time;

analysis means having access to said memory means for analyzing said periodic physiological signal using the samples stored in said memory means by estimating a number of said physiological events occurring in said periodic physiological signal during said time and for generating a first set of values corresponding to said physiological events;

said analysis means including means for calculating at least one derived parameter from said first set of values;

said analysis means including means for automatically determining a first new threshold detection level for said sampling means as a function of said at least one derived parameter; and said analysis means including means for calculating a plurality of further new threshold detection levels which differ from said first new threshold detection level by a plurality of different amounts and for comparing each of said further new threshold detection levels with said samples stored in said memory means for determining how many physiological events would have been detected if each further new threshold level had been used by said sampling means during said time and for setting the threshold detector level of said sampling means to one of said first and further new threshold detector levels which would have detected said estimated number of physiological events.

11. A medical diagnostic device as claimed in claim 10 wherein said means for calculating a plurality of further new threshold detection levels comprises means for calculating a plurality of further new threshold detection levels which differ from the first new threshold detection level by a plurality of predetermined different amounts.

12. A medical diagnostic device as claimed in claim 10 wherein said means for calculating a plurality of further new threshold detection levels comprises means for calculating a plurality of further new threshold detection levels which differ from the first new threshold detection level by a plurality of programmable different amounts.

13. A medical diagnostic device as claimed in claim 10 wherein said set of values comprises a first set of values, and said analysis means further including:

discriminating means for ignoring at least one value of said first set of values and for forming a second set of values comprising said first set of values without said at least one value;

means for calculating at least one auxiliary derived parameter from said second set of values; and means for automatically varying said threshold detection level of said sensor means as a function of said at least one auxiliary derived parameter and said derived parameter.

14. A medical diagnostic device as claimed in claim 13 wherein said means for calculating at least one auxiliary derived parameter from said second set of values comprises means for determining an average peak signal value.

15. A medical diagnostic device as claimed in claim 13 wherein said means for calculating at least one auxiliary derived parameter from said second set of values comprises means for determining an average maximum signal slope.

16. A medical diagnostic device as claimed in claim 13 wherein said means for calculating at least one auxiliary derived parameter from said second set of values comprises means for determining an integrated signal value.

17. A medical diagnostic device as claimed in claim 13 wherein said discriminating means comprises means for ignoring a maximum value in said first set of values.

18. A medical diagnostic device as claimed in claim 13 wherein said discriminating means comprises means for ignoring a minimum value in said first set of values.

19. A medical diagnostic device as claimed in claim 13 wherein said discriminating means comprises means for determining an average value of said first set of values and means for ignoring a value of said first set of values which is farthest from said average value.

20. A medical diagnostic device as claimed in claim 10 wherein said sensor means comprises means for sensing a cardiac signal, representing cardiac events, from said living subject and wherein said analysis means estimates a number of said cardiac events.

21. A method for setting a threshold detection level in a medical diagnostic device comprising the steps of:

sensing a periodic physiological signal, representing physiological events, from a living subject;

sampling said periodic physiological signal by employing a threshold detection level;

storing samples of said periodic physiological signal;

stopping said sampling after a predetermined time;

analyzing said periodic physiological signal using the stored samples by estimating a number of said physiological events occurring in said periodic physiological signal during said time and generating a set of values corresponding to said physiological events;

calculating at least one derived parameter from said set of values; and automatically determining a new threshold detection level for said sampling as a function of said at least one derived parameter and means for comparing said new threshold detection level with the stored samples for determining how many of said physiological events would have been detected if said new threshold detection level had been used in said sampling, and changing said threshold detection level of said sampling to said new threshold detection level if the number of physiological events which would have been detected differs by more than a programmable number from said estimated number of physiological events.

22. A method as claimed in claim 21 wherein said set of values comprises a first set of values, and comprising the further steps of:

ignoring at least one value of said first set of values and forming a second set of values comprising said first set of values without said at least one value;

calculating at least one auxiliary derived parameter from said second set of values; and automatically varying said threshold detection level of said sensor means as a function of said at least one auxiliary derived parameter and said derived parameter.

23. A method as claimed in claim 22 wherein the step of calculating at least one auxiliary derived parameter from said second set of values comprises determining an average peak signal value.

24. A method as claimed in claim 22 wherein the step of calculating at least one auxiliary derived parameter from said second set of values comprises determining an average maximum signal slope.

25. A method as claimed in claim 22 wherein the step of calculating at least one auxiliary derived parameter from said second set of values comprises determining an integrated signal value.

26. A method as claimed in claim 22 wherein the step of ignoring at least one value comprises ignoring a maximum value in said first set of values.

27. A method as claimed in claim 22 wherein the step of ignoring at least one value comprises ignoring a minimum value in said first set of values.

28. A method as claimed in claim 22 wherein the step of ignoring at least one value comprises determining an average value of said first set of values and ignoring a value of said first set of values which is farthest from said average value.

29. A method as claimed in claim 21 Wherein the step of sensing a periodic physiological signal comprises sensing a cardiac signal, representing cardiac events, from said living subject, and wherein the step of analyzing said periodic physiological signal comprises analyzing said cardiac signal and estimating a number of said cardiac events therein.

30. A method for setting a threshold detection level in a medical diagnostic device comprising the steps of:

sensing a periodic physiological signal, representing physiological events from a living subject;

sampling said periodic physiological signal employing a threshold detection level by employing a threshold detection level;

storing samples of said periodic physiological signal;

stopping said sampling after a predetermined time;

analyzing said periodic physiological signal using the stored samples by estimating a number of said physiological events occurring in said periodic physiological signal during said time and generating a first set of values corresponding to said physiological events;

calculating at least one derived parameter from said first set of values;

automatically determining a first new threshold detection level for said sampling as a function of said at least one derived parameter; and calculating a plurality of further new threshold detection levels which differ from said first new threshold detection level by a plurality of different amounts and comparing each of said further new threshold detection levels with said stored samples for determining how many physiological events would have been detected if each further new threshold level had been used in said sampling during said time and for setting the threshold detection level of said sampling to one of said first and further new threshold detector levels which would have detected said estimated number of physiological events.

31. A method as claimed in claim 30 wherein said set of values comprises a first set of values, and comprising the further steps of:

ignoring at least one value of said first set of values and forming a second set of values comprising said first set of values without said at least one value;

calculating at least one auxiliary derived parameter from said second set of values; and automatically varying said threshold detection level of said sensor means as a function of said at least one auxiliary derived parameter and said derived parameter.

32. A method as claimed in claim 31 wherein the step of calculating at least one auxiliary derived parameter from said second set of values comprises determining an average peak signal value.

33. A method as claimed in claim 31 wherein the step of calculating at least one auxiliary derived parameter from said second set of values comprises determining an average maximum signal slope.

34. A method as claimed in claim 31 wherein the step of calculating at least one auxiliary derived parameter from said second set of values comprises determining an integrated signal value.

35. A method as claimed in claim 31 wherein the step of ignoring at least one value comprises ignoring a maximum value in said first set of values.

36. A method as claimed in claim 31 wherein the step of ignoring at least one value comprises ignoring a minimum value in said first set of values.

37. A method as claimed in claim 31 wherein the step of ignoring at least one value comprises determining an average value of said first set of values and ignoring a value of said first set of values which is farthest from said average value.

38. A method as claimed in claim 30 wherein the step of sensing a periodic physiological signal comprises sensing a cardiac signal, representing cardiac events, from said living subject, and wherein the step of analyzing said periodic physiological signal comprises analyzing said cardiac signal and estimating a number of said cardiac events therein.

* * * * *